United States Patent [19]
Moret

[11] 4,138,064
[45] Feb. 6, 1979

[54] RINSING DEVICE FOR PERSONAL HYGIENE

[75] Inventor: Michel Moret, Chene-Bourg, Switzerland

[73] Assignee: Les Produits Associes LPA S.A., Geneva, Switzerland

[21] Appl. No.: 849,301

[22] Filed: Nov. 7, 1977

Related U.S. Application Data

[62] Division of Ser. No. 761,269, Jan. 21, 1977.

[30] Foreign Application Priority Data

Jan. 21, 1976 [CH] Switzerland ............................ 708/76

[51] Int. Cl.² .............................................. F16K 3/14
[52] U.S. Cl. .................................. 239/582; 222/521; 251/346; 251/353
[58] Field of Search ............... 239/101, 102, 569, 579, 239/581, 582; 251/346, 347, 353; 222/521; 128/66

[56] References Cited
U.S. PATENT DOCUMENTS

| | | | |
|---|---|---|---|
| 1,904,739 | 4/1933 | Kroen | 222/521 |
| 2,855,930 | 10/1958 | Blankfield | 128/66 UX |
| 3,771,517 | 11/1973 | Radecki | 128/66 |

Primary Examiner—Robert W. Saifer
Attorney, Agent, or Firm—Kane, Dalsimer, Kane, Sullivan and Kurucz

[57] ABSTRACT

A nozzle assembly for coupling with the outlet of a rinsing device. The assembly includes a two-part nozzle holder, with one part having a pair of diametrically opposite grooves. Each of the grooves has one groove section inclined to the axis of the nozzle holder and a second groove section which merges into the first. The second section is oriented perpendicular to the axis of the nozzle holder. The other part of the nozzle holder includes a pair of projections deposed in the grooves. Rotation of one part of the holder with respect to the other causes a valve assembly to open and close. The valve assembly includes an internal pin within the nozzle assembly. The pin has a rounded head and forms the closing member. It is situated within a flow passage defined by a bushing having an inner sleeve. Axial grooves may be provided to facilitate assembly of the two-part nozzle.

3 Claims, 11 Drawing Figures

U.S. Patent  Feb. 6, 1979  Sheet 3 of 4  4,138,064
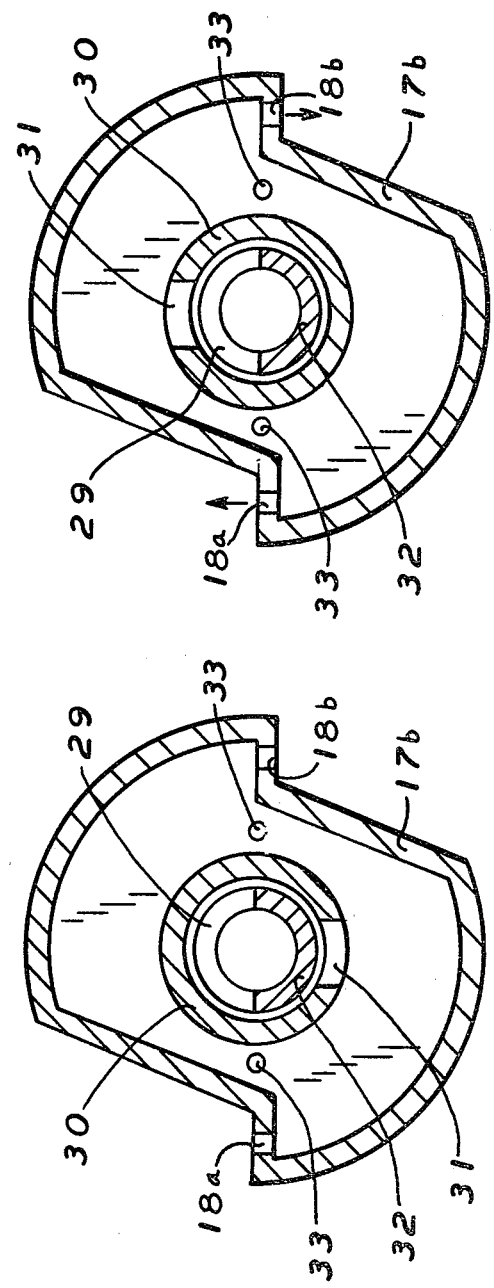

RINSING DEVICE FOR PERSONAL HYGIENE

CROSS REFERENCE TO RELATED APPLICATION

This application is divisional application of Ser. No. 761,269, filed Jan. 21, 1977.

BACKGROUND OF THE INVENTION

Known rinsing devices which are generally intended for connection to the water tap of a water pipe have the disadvantage that the amount of water emerging from the spray nozzle and available for the liquid treatment is reduced by that proportion which is needed to drive the turbine and which constantly emerges from the turbine jet openings and through corresponding discharge openings. As a result, the liquid pulses produced, even with a comparatively high tap water pressure are not so powerful and sharp as is desirable for effective treatment. In addition, in the known rinsing devices working with turbines, the turbine speed increases substantially linearly with the pressure of the tap water. Therefore, if the user increases the water pressure, that is to say turns the water tap on further then the pulse repetition frequency of the pulsating jet of liquid produced also increases in an unfavorable manner.

SUMMARY OF THE INVENTION

The principal object of the invention is to provide a rinsing device of the kind described which is easily connected to a water pipe, so that the amount of water available for liquid treatment is increased and a pulsating liquid jet is produced with more powerful and sharply pronounced pulses, as a result of which the effectiveness of the liquid massage, rinsing and/or cleansing is increased.

Toward this end, the rinsing device according to this invention includes a further rotary valve disposed in the conduit leading from the pressure-water passage to the jet opening. The rotating element of this valve is rapidly connected to the rotating part of the first rotating valve and which is adapted to block this conduit intermittently each time, at least approximately during that interval of time when the first rotary valve is passing through its open position.

As a result, during the period that the outlet is open, the entire amount of water supplied is available to produce the liquid pulses, the power of which is thus increased accordingly; this effect of producing sharper liquid pulses is enhanced by the repeated backing-up effect in the pressure-water passage as a result of the blocking of the turbine feed. In this manner, the rinsing device according to the invention permits a more effective liquid massage and rinsing than devices hitherto known and, particularly in the case of a mouthwashing device, a particularly satisfatory massage of the gums and an effective cleaning and rinsing of the teeth and the gaps therebetween is attained.

In addition, it has been found that with the rinsing device according to the invention, the turbine speed advantageously only increases with the water pressure up to a specific, comparatively low pressure of the feed water, but then remains substantially constant as the water pressure rises further. In an embodiment of the rinsing device according to the invention, the turbine speed rose with rinsing water pressure only up to a pressure of about 2-2.5 bar up to about 2,500 r.p.m. and then remained approximately constant as the water pressure rose further, being increased to about 10 bar, that is to say about 10 at. This has the great advantage that the pulse repetition frequency of the liquid pulses remains substantially constant in the range of the pressure generally used in practice for the liquid treatment. It is believed that this extremely advantageous effect results essentially from the intermittent feed of the turbine.

Known rinsing devices equipped with a thrust bearing for the turbine further have the disadvantage that this thrust bearing is heavily loaded under the action of the pressure of the water flowing in the direction of the turbine axis, generally through a hollow turbine shaft, and the comparatively great friction thus produced has an adverse effect on the running of the small turbine. In order to largely avoid this problem, the present invention when equipped with a thrust bearing for the turbine, provides the turbine surface which is adjacent to the thrust bearing which preferably consists of a ball and a contact surface for the ball, is preferably provided with wing-like projections which, on rotation of the turbine, produce a force which counteracts the force urging the turbine towards the thrust bearing. Furthermore, the turbine wall adjacent to the said bearing can be provided with axial channels through which water jets can pass with a force that also counteracts the frictional force of the thrust bearing. These axially directed jets have been found to function as a sort of velocity regulator which creates a braking effect which contributes to holding constant the speed of rotation of the turbine. Also the internal pressure is reduced which is also quite useful.

In a rinsing device according to the invention a nozzle holder is provided which can be connected to a connecting tube for the interchangeable attachment of a spray nozzle. The nozzle holder consists of two coaxial parts which are capable of being turned or screwed through a limited angle between two positions. A shut-off valve within the holder closes a flow passage in one position and in the other position opens it. The screw connection preferably comprises on the one part diametrically opposite grooves with a groove section oriented obliquely to the axis of the nozzle holder and a peripheral groove section orientated perpendicular to the axis of the nozzle holder and defining the closed position, and on the other part projections which engage in these grooves.

BRIEF DESCRIPTION OF THE DRAWINGS

In the drawings:

FIGS. 3a and 3b show cross-sectional views through the two rotary valves, namely, through the liquid pulse generator of FIG. 2 at the height of the outlet (FIG. 3a) and through its turbine (FIG. 3b);

FIGS. 4a and 4b are similar views with the outlet closed and the turbine feed released;

FIG. 8 shows a side view of the handle portion of the nozzle holder; and

FIG. 9 shows a plan view of the front end face of the handle portion of FIG. 8.

DETAILED DESCRIPTION

Figure 1:
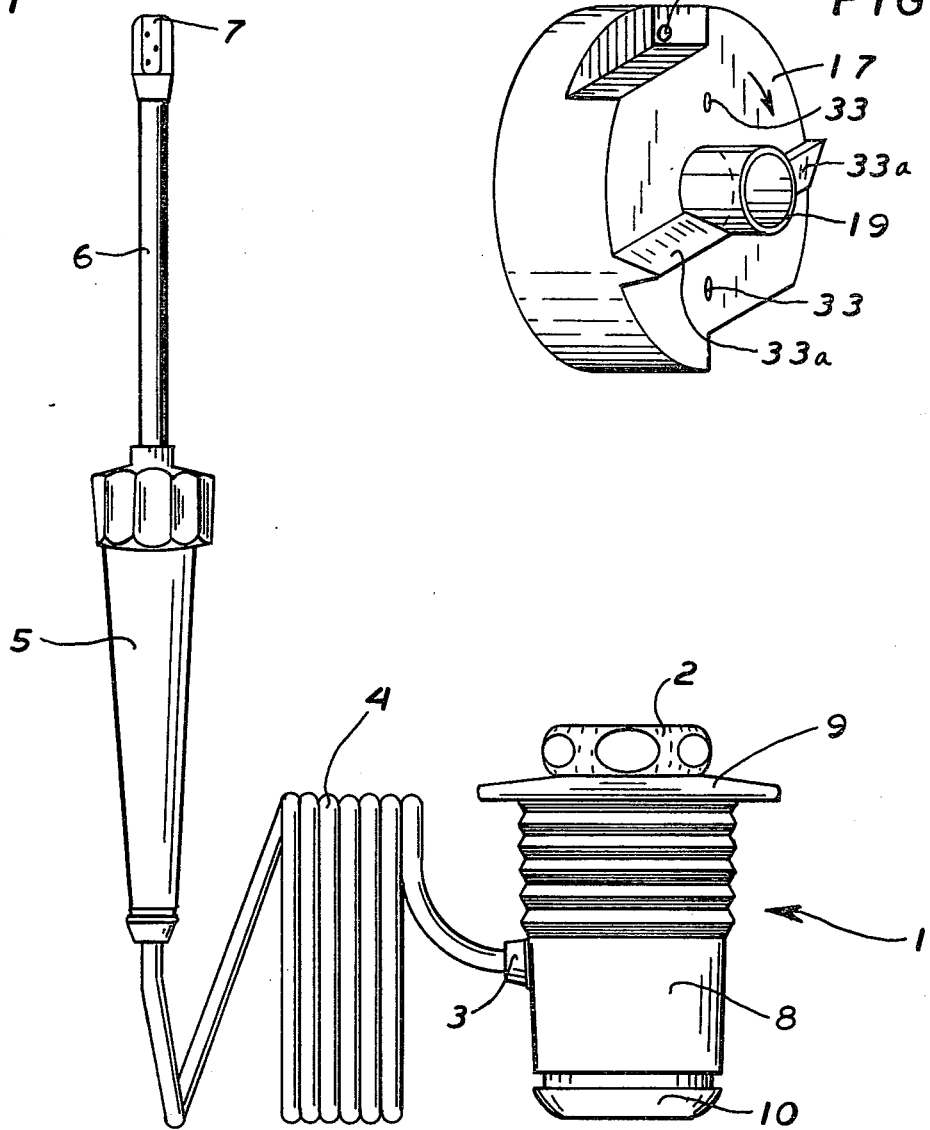
FIG. 1 shows a diagrammatic view of the rinsing device of this invention.
Figure 5:
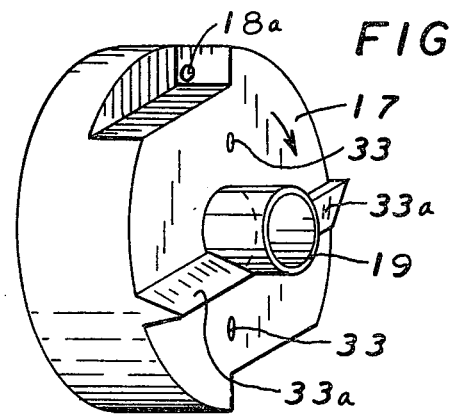
FIG. 5 shows a perspective view of the side of the turbine adjacent to the thrust bearing.

Referring initially to FIG. 1, the rinsing device of the present invention comprises a liquid pulse generator 1, which can be connected, by its inlet socket 2, to any desired source of pressure water, particularly to the tap of a water pipe.

The socket 3 at the outlet of the liquid pulse generator 1 is connected by a flexible tube 4 to a spray-nozzle holder 5 which has a handle portion and carries an interchangeable spray nozzle with the nozzle tube 6 and the nozzle head 7 located at the discharge end.

Figure 2:
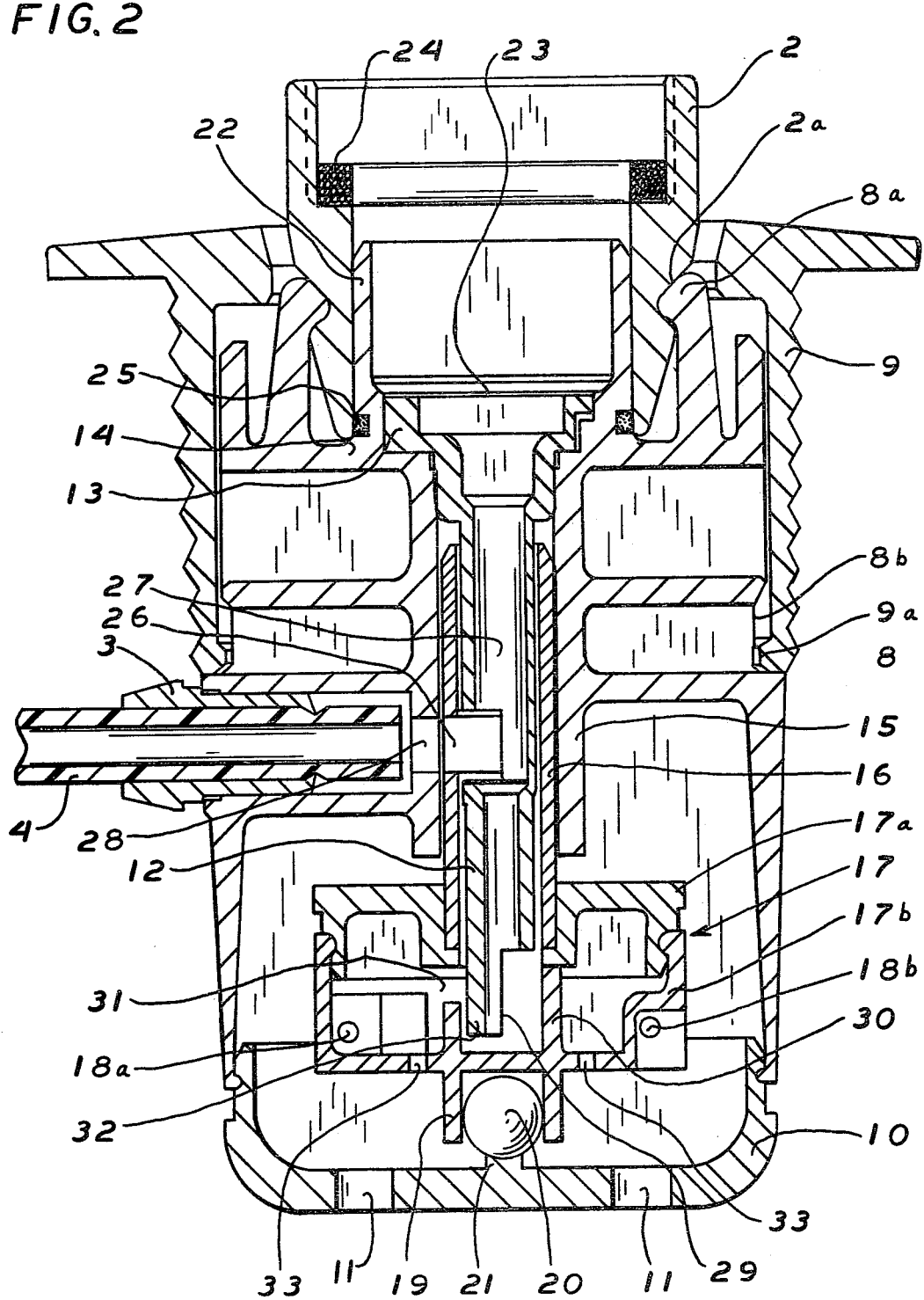
FIG. 2 shows a longitudinal axial section through the liquid pulse generator.
Figure 6:
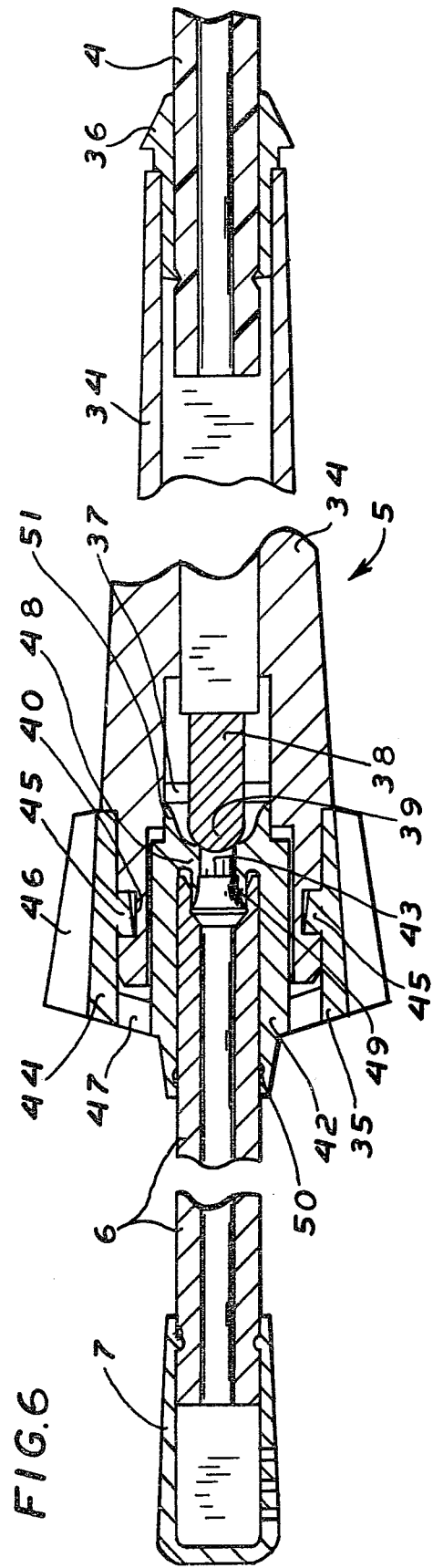
FIG. 6 shows a longitudinal section through the nozzle holder with superimposed spray nozzle and with the shut-off valve in the closed position.
Figure 7:
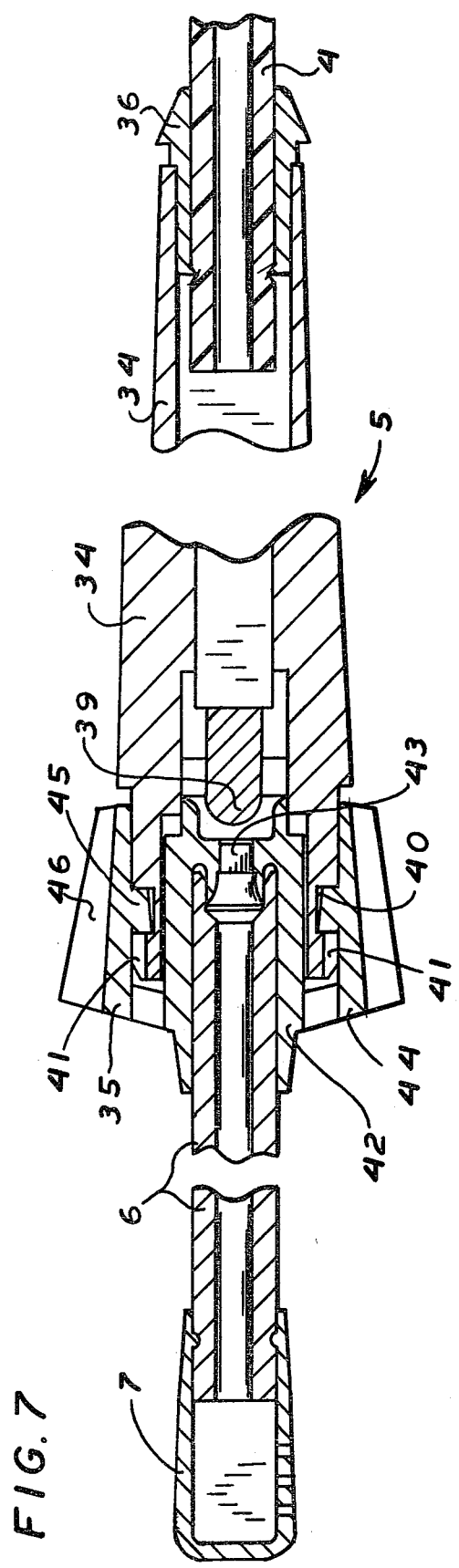
FIG. 7 is a similar section with the shut-off valve in the open position.

Referring now to FIG. 2, the liquid pulse generator 1 has a housing body 8, which receives at its inlet side an inlet socket 2, held by a locking sleeve 9 and resilient locking tongues 8a of the housing body 8 which is pressed into corresponding recesses 2a at the periphery of the inlet socket 2. The locking sleeve 9 is held captive by resilient engagement of a radial inwardly extending flange 9a in an annular groove 8b at the periphery of the housing body 8, but is movable axially between the locking position shown in FIG. 2 and an unlocking position which releases the locking tongues 8a and in which it is displaced upwards in comparison with the position in FIG. 2.

The open side of the housing body 8, remote from the inlet, is covered by a resiliently coupled cap 10 which is provided with water discharge openings 11.

An axial hollow pin 12 is secured at its end 13, in a correspondingly stepped inner wall region 14 of the housing body 8. Pin 12 is surrounded by an internal sleeve 15, forming an annular chamber and carries a rotatably mounted turbine shaft 16 with a turbine 17.

An annular ring 22 extends from wall region 14 and about which the inlet socket 2 is mounted. A grating or screen 23 is disposed at the opening of the hollow pin 12 with ring 22. Wall region 14, internal sleeve 15 and annular ring 22 are integral parts of the housing body 8. A sealing ring 24 is provided in the inlet socket 2 and a further sealing ring 25 is provided between the inlet socket 2 and the housing. When the inlet socket 2 is connected to a water pipe, water under pressure flows into the hollow pin 12, the interior of which forms the pressure-water passage.

The turbine 17, which is secured to the turbine shaft 16, is constructed in a manner depicted in FIGS. 2, 3b, 4b and 5. In this connection, the turbine 17 is in the form of a hollow wheel into which the interior of the hollow pin 12 leads. The turbine 17 comprises, at its periphery, two diametrically opposite, tangentially orientated jet openings 18a and 18b. For manufacturing reasons, the turbine 17 is composed of two bowl-shaped portions 17a and 17b. The outer wall of the turbine portion 17b, comprises a central, hollow cylindrical extension 19 in which there is a ball 20. The ball 20 can bear against a bearing surface 21 (FIG. 2) which is formed on the inside of the cap 10 in the form of a cylindrical projection that has a smaller diameter than ball 20. In this manner, ball 20 and bearing surface 21 form a thrust bearing for the turbine 17, when urged towards the cap 10, during operation, under the effect of the water pressure.

The bearing surface 21 is provided with a small slightly conical recess so as to correctly center the ball 20. When the apparatus is first used, the ball 20 is centered on the bearing surface 21 and bears on the circular edge of this conical recess. When the apparatus has been used for some time, there is a "running-in" effect, in that the circular edge of the recess is worn away by friction until there is formed a cavity adapted to the curvature of the ball; however, this effect has practically no disadvantage as centering is still maintained, and the friction remains constant after "running-in" since the diameter of the circular bearing face 21, defined by the diameter of the cylindrical projection, always remains the same.

As shown in FIG. 2, the length of the hollow turbine shaft 16 is so dimensioned in relation to the length of the hollow pin 12 that the turbine 17 together with its shaft 16 has axial clearance.

Figure 3A:
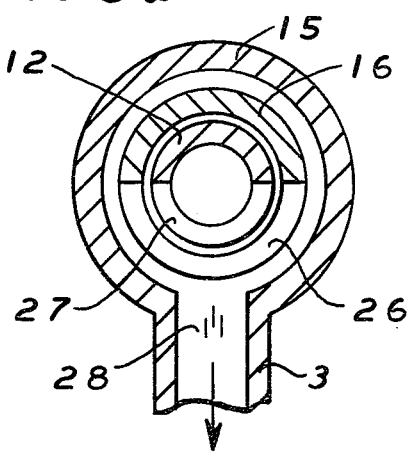
Figure 4A:
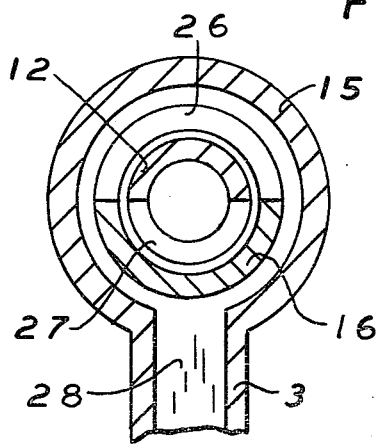

According to FIGS. 2, 3a and 4a, the peripheral wall of the hollow turbine shaft 16 comprises an aperture 26 which, when the turbine shaft is in the position illustrated in FIGS. 2 and 3a, is in alignment with an opening 27 provided in the wall of the hollow pin 12 and an outlet 28 which is provided in the wall of the internal sleeve 15 and which leads into the radial outlet socket 3 with the attached tube 4. Therefore, the turbine shaft 16 in conjunction with the opening 27 in the hollow pin 12, simultaneously forms the valve body and the aperture 26 forms the valve opening of a rotary valve. When the turbine is rotating, the shaft 16 only permits discharge through the outlet 28 or the outlet socket 3 intermittently and so produces a pulsating jet of liquid conveyed through the tube 4 to the spray nozzle.

The end of the hollow pin 12 leading into the interior of the turbine 17 has, according to FIGS. 2, 3b and 4b a recess 29 at its periphery and is surrounded by an internal, sleeve-shaped wall portion 30 of the turbine 17, which is provided with a peripheral opening 31. The arrangement is such that this opening 31 is always covered by the wall section 32 of the hollow pin 12 whenever the aperture 26 in the turbine shaft 16 releases the liquid outlet to the spray nozzle; on the other hand, the opening 31 is only in alighment with the recess 29 in the hollow pin 12 and therefore only permits a feed of the slide openings 18a and 18b of the turbine with pressure water, when the outlet 28 is blocked. Thus, the opening 31 in the turbine 17, in conjunction with the wall section 32 of the hollow pin 12, forms the valve opening of a further rotary valve, which has a common valve body with the first-mentioned rotary valve, namely the turbine shaft, and only adopts its open position when the first-mentioned rotary valve is in its closed position. The aperture 26 in the turbine shaft 16, the opening 27 in the wall of the hollow pin 12 and the recess 29 at the end of the hollow pin extend at least substantially over an arc of a semicircle, while the outlet 28 and the opening 31 in the interior of the turbine 17 occupy a considerably smaller peripheral region (see FIGS. 3a, 3b, 4a and 4b). In this manner, practically the whole amount of pressure water supplied is available to feed the spray nozzle whenever the outlet 28 or the outlet socket 3 is open because the turbine feed is interrupted. In addition, as has been found, the intermittent feed of the turbine 17 contributes to the fact that the turbine speed practically no longer rises with a rising water pressure above a comparatively low water pressure which, in a successful embodiment was about 2.5 bar, but remains approximately constant and, in this embodiment was about 2,500 r.p.m. This has the advantage that, with the water pressures which are generally available and within the pressure ranges generally used by the user, the turbine speed and hence the pulse repetition frequency of the pulsating jet of liquid produced is at least approximately constant.

The liquid pulse generator 1 is normally connected to the water tap over a wash-basin and then has its axis or its pressure-water passage in a vertical position, with the cap 10 facing downwards and situated above the drain of the wash-basin. The liquid flowing through the pressure-water passage in the hollow pin 12 and the interior of the turbine 17 emerges from the jet openings 18a and 18b of the turbine 17, as indicated by the arrows F in FIG. 4b. As a result the turbine is set in rotation by reaction. The water emerging from the turbine and reaching the lower region of the housing can run away through the discharge openings 11 in the cap 10. A pulsating jet of liquid, feeding the attached spary nozzle, as indicated by the arrow F in FIG. 3a, is produced in the outlet 28, as described, by the rotating turbine shaft 16 together with its aperture 26. In the example shown in FIG. 2, the internal diameter of the hollow pin 12 and hence the cross-section of the pressure-water passage becomes narrower immediately behind the opening 27, as a result of which a certain damming up of liquid is produced at this point, through which the amount of liquid emerging from the outlet 28 is increased.

In order to reduce the severe friction occurring under the action of the comparatively high liquid pressure, between the ball 20 and the bearing surface 21, and so to relieve the thrust bearing of the turbine, two wing-like extensions 33a (FIG. 5) are formed on the outer face of the turbine 17 adjacent to the thrust bearing, namely, on the outer wall of the turbine portion 17b. Accordingly, upon rotation of the turbine, an axial force is produced which tends to lift the turbine from the bearing surface 21. According to FIG. 5 the two wing-like extensions 33a are formed diametrically opposite at both sides of the hollow cylindrical projection 19. These extensions 33a in the form of radial ribs have a triangular cross-section, the surfaces which face in the direction of rotation of the turbine and in the direction of the arrow of FIG. 5, being inclined obliquely to the plane of rotation of the turbine.

In addition, the same turbine wall is provided with diametrically-opposed axial channels 33 through which a small quantity of water escapes. Tests have shown that these weak jets of water, which issue axially with a given force from the lower face of the turbine, act as a kind of speed regulator by providing a braking effect so that over and above a given pressure of water supply, the holding constant of the speed of rotation of the turbine is further improved.

As a result of both the wing-like extensions 33a and the axial jets through the axial channels 33, the thrust-bearing friction is reduced and the effect is achieved that the turbine runs more easily and also more uniformly than in devices of this kind hitherto known.

FIGS. 6–9 show the mounting of the nozzle holder 5 for the spray nozzle which can be attached interchangeably. This nozzle holder is constructed in two parts and consists of an elongated hollow handle portion 34 and a bushing 35 which is mounted on its front end for screwing within a limited angle and in which the spray nozzle 6, 7 can be inserted. The rotation of tube 6 relative to the handle portion 34 causes the shutting off or the opening of a shut-off valve in the nozzle holder between end positions.

The rear end of the hollow handle portion 34 is connected to the flexible tube 4 by means of a connecting piece 36. In the front region, the handle portion 34 comprises a central pin 38 which is connected to the peripheral wall by radial ribs 37 (FIG. 9) and forms, with its head 39, the closing member of the shut-off valve. The front region of the peripheral wall of the handle portion 34 has, at its outside, two diametrically opposite angled grooves 40 (FIG. 8) with each comprising a groove section 40a which is orientated obliquely to the axis of the handle portion and forms part of a screw thread and which merges into a groove secton 40b extending substantially perpendicular to the axis of the handle portion. The end of the oblique groove section 40a of each of the grooves 40, adjacent to the front of the handle portion 34, leads into an axial portion 41 and the depth of which is somewhat less than the depth of the angled grooves 40. For manufacturing reasons, the handle portion 34 is preferably moulded in two parts: an outer tubular part which forms the gripping part of the handle and in which is elastically clip-fitted an inner part comprising the valve elements and the screw-thread-shaped groove 40.

The bushing 35 consists of an inner sleeve 42 and an outer sleeve 44 which together are made integral and are connected to one another, in the front region, by a radial wall 47 which comprises at least two openings for manufacturing reasons. The inner sleeve 42 receives the tube 6 of the spray nozzel 6, 7 and comprises, at its rear, the flow passage 43 of said shut-off valve, which cooperates with the closing member 39 of the handle portion 34. The outer sleeve 44 has, at its interior, two diametrically opposite projections 45 which are disposed in the grooves 40, and which are of a width approximating that of the grooves 40. The outer periphery of the outer sleeve 44 is provided with a knurling 46.

The inner sleeve 42 includes at its rear an annular shoulder 48 which projects radially inwards and which defines the flow passage 43 of the shut-off valve. This shoulder 48 also forms the seating surface for the closing member 39 at its rear and terminates in an annular lip 49 at its front. The rear end of the tube 6 of the spray nozzle engages in the annular space surrounding this annular lip 49 and, in this manner, can be inserted tightly in the bushing 35 and held by means of a resiliently flexible engagement projection 50 which is formed at the inner periphery of the inner sleeve 42 and engages in a corresponding notch at the periphery of the nozzle tube 6. The tight connection between bushing 35 and handle portion 34 is achieved by means of an annular lip 51 which is formed at the rear end of the internal sleeve 42 of the bushing 35.

By turning the handle portion 34 relatively to the bushing 35, the projections 45 on the bushing are accordingly shifted into the guiding grooves 40 in the handle portion 34. In the shut-off position illustrated in FIG. 6, the closing member 39 blocks the flow passage 43 while bearing against the valve seat and the projections 45 on the bushing 35 are inside the peripheral inner groove section 40b. In the open position illustrated in FIG. 7, the flow passage 43 is open and the projections 45 are at the front end of the oblique groove section 40a. A reliable and stable closing position of the shut-off valve is achieved by the peripheral inner groove section 40b defining the closed position. As soon as the projections 45 reach the oblique groove section 40a, during rotation into the open position, the shut-off valve automatically adopts its open position if the water pressure is sufficiently strong.

In order to assemble the nozzle holder 5 from the two parts 34 and 35, it is sufficient to slide the bushing 35 onto the handle portion 34, with engagement of the projections 45 in the axial grooves 41. The sliding motion is continued until the projections 45 engage in the grooves 40 which, as mentioned, have a somewhat greater depth than the axial grooves 41, so that now the bushing 35 can no longer simply be detached from the handle portion 34. In order to facilitate this sliding of the bushing 35 onto the handle portion 34 during assembly, the inner faces of the projections 45 are bevelled relative to the axis of the handle portion in such a manner that they are inclined outwardly in a rearward direction.

Thus, the nozzle holder 5 can be assembled of a suitable plastics material, very simply and without separate attachment means. The same applies to the liquid pulse generator which, with the exception of the ball 20 and preferably the turbine shaft 16 and the grating 23, which consist of metal, is composed of plastics parts. All the parts of the generator are capable of being connected to one another without using separate attachment members, either by resilient interengagement or by a force fit. Thus, the rinsing device according to the invention produces sharper liquid pulses with comparatively greater amounts of water while relieving the thrust bearing of the turbine but also is of simple construction and easily assembled at reduced costs.

Instead of only one aperture 26 in the turbine shaft 16 and only one opening 31 in the inner sleeve 30 of the turbine, two or more rotating valve openings may be provided in each case so that the outlet 28 is released several times and the turbine feed is correspondingly interrupted several times during each complete revolution of the turbine.

What is claimed is:

1. A nozzle assembly for coupling with the outlet of a rinsing device for personal hygiene, particularly for mouth washing, the assembly comprising a nozzle holder and means for interchangeably attaching a nozzle to the holder, the nozzle holder comprised of two coaxial parts screwed in relation to one another over a limited angle between two positions, one of which parts include a flow passage and the other including a closing member which cooperates with the flow passage in defining a shut-off valve and which in the one position blocks the flow passage and in the other position opens it, one of the two parts forming the nozzle holder including a cylindrical region at its outer periphery, a plurality of diametrically opposite grooves in the cylindrical region, each of which has a groove section inclined to the axis of the nozzle holder, which section at one end merges into another groove section extending at least approximately peripherally and orientated perpendicular to the axis of the nozzle holder, the other part of the nozzle holder comprising a number of projections corresponding to the number of grooves and being disposed therein, and one of the parts of the nozzle holder being an elongated hollow handle portion and comprising an internal pin situated inside the flow passage, the pin provided with a rounded head forming the closing member, and the other part comprising a bushing having an inner sleeve forming the flow passage of the shut-off valve and adapted to receive a nozzle tube of the spray nozzle and an outer sleeve which is made integral with the inner sleeve and at the internal periphery of which there are formed the projections disposed in the grooves.

2. A nozzle assembly according to claim 1, wherein the inner faces of the projections on the bushing extend inclined outwards in the backward direction in relation to the axis of the nozzle holder.

3. A nozzle assembly for coupling with the outlet of a rinsing device for personal hygiene, particularly for mouth wasing, the assembly comprising a nozzle holder and means for interchangeably attaching a nozzle to the holder, the nozzle holder comprised of two coaxial parts screwed in relation to one another over a limited angle between two positions, one of which parts includes a flow passage and the other including a closing member which cooperates with this flow passage in defining a shut-off valve and which in the one position blocks the flow passage and in the other position opens it, one of the two parts forming the nozzle holder including a cylindrical region at its outer periphery, a plurality of diametrically opposite grooves in the cylindrical region, each of which has a groove section inclined to the axis of the nozzle holder, which section at one end merges into another groove section extending at least approximately peripherally and oriented perpendicular to the axis of the nozzle holder, the other part of the nozzle holder comprising a number of projections corresponding to the number of grooves and being disposed therein, and one of the parts of the nozzle holder being an elongated hollow handle portion, axial grooves being provided at the external periphery of the handle portion, said axial grooves having a smaller depth than the groove sections and branching off therefrom, said axial grooves extending as far as the front end of the handle portion, whereby in assembling the two parts of the nozzle assembly, one part can be pushed onto the handle portion with engagement of the projections in the axial grooves until said projections engage in said groove sections.

* * * * *